United States Patent
Suhr

[19]

[11] Patent Number: 5,849,016
[45] Date of Patent: Dec. 15, 1998

[54] CATHETER EXCHANGE METHOD AND APPARATUS

[76] Inventor: William S. Suhr, 14 Shoreside, South Barrington, Ill. 60010

[21] Appl. No.: 759,979

[22] Filed: Dec. 3, 1996

[51] Int. Cl.[6] ......................................................... A61F 11/00
[52] U.S. Cl. ............................................. 606/108; 600/585
[58] Field of Search ..................................... 606/108, 194, 606/192; 600/585; 604/96

[56] References Cited

U.S. PATENT DOCUMENTS

| | | |
|---|---|---|
| 5,255,690 | 10/1993 | Keith et al. . |
| 5,312,338 | 5/1994 | Nelson et al. ............................ 600/585 |
| 5,454,785 | 10/1995 | Smith . |
| 5,460,185 | 10/1995 | Johnson et al. ........................... 600/585 |
| 5,487,729 | 1/1996 | Avellanet et al. ......................... 600/585 |

*Primary Examiner*—Michael Buiz
*Assistant Examiner*—Kevin Truong
*Attorney, Agent, or Firm*—Lawrence Cruz

[57] ABSTRACT

A method and apparatus for installing, removing or exchanging catheters into and out of a medical patient's body, including the vascular system, incorporates a slotted guide track for guiding and controlling sliding movement of a catheter while maintaining the relative position of a guidewire. The guide track includes an elongated base having a resilient, cushion-like body, adapted to physically conform to the outer shape of a guidewire and catheter to accommodate the passing through of a catheter and related structures. The guide track includes a clamp at one end for securing a guidewire end, and another clamp at the other end for securing the track to a guide catheter.

20 Claims, 4 Drawing Sheets

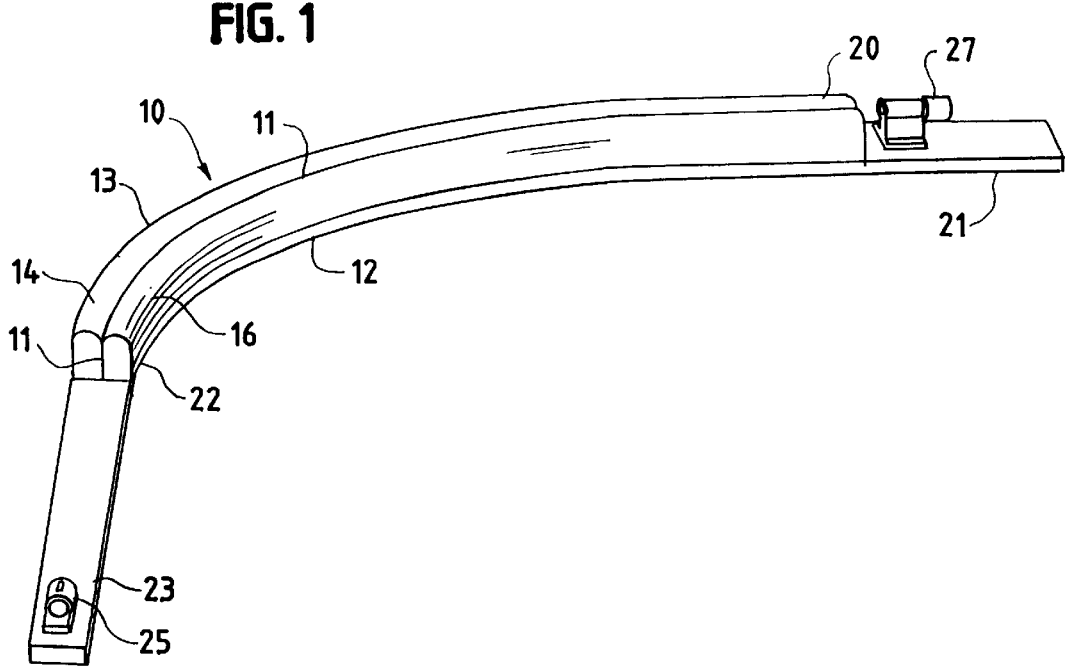
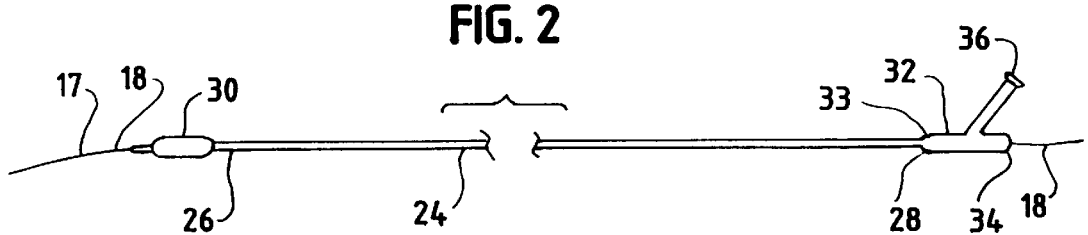
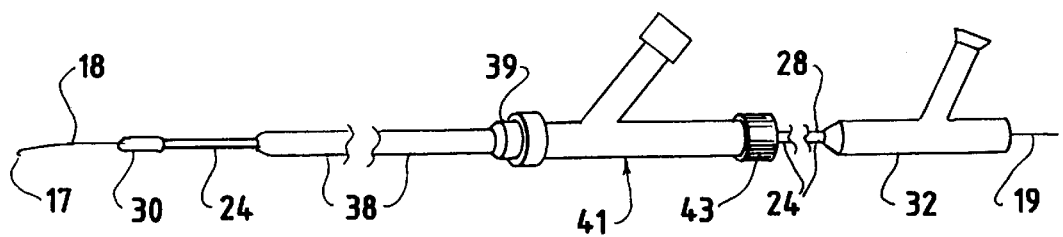

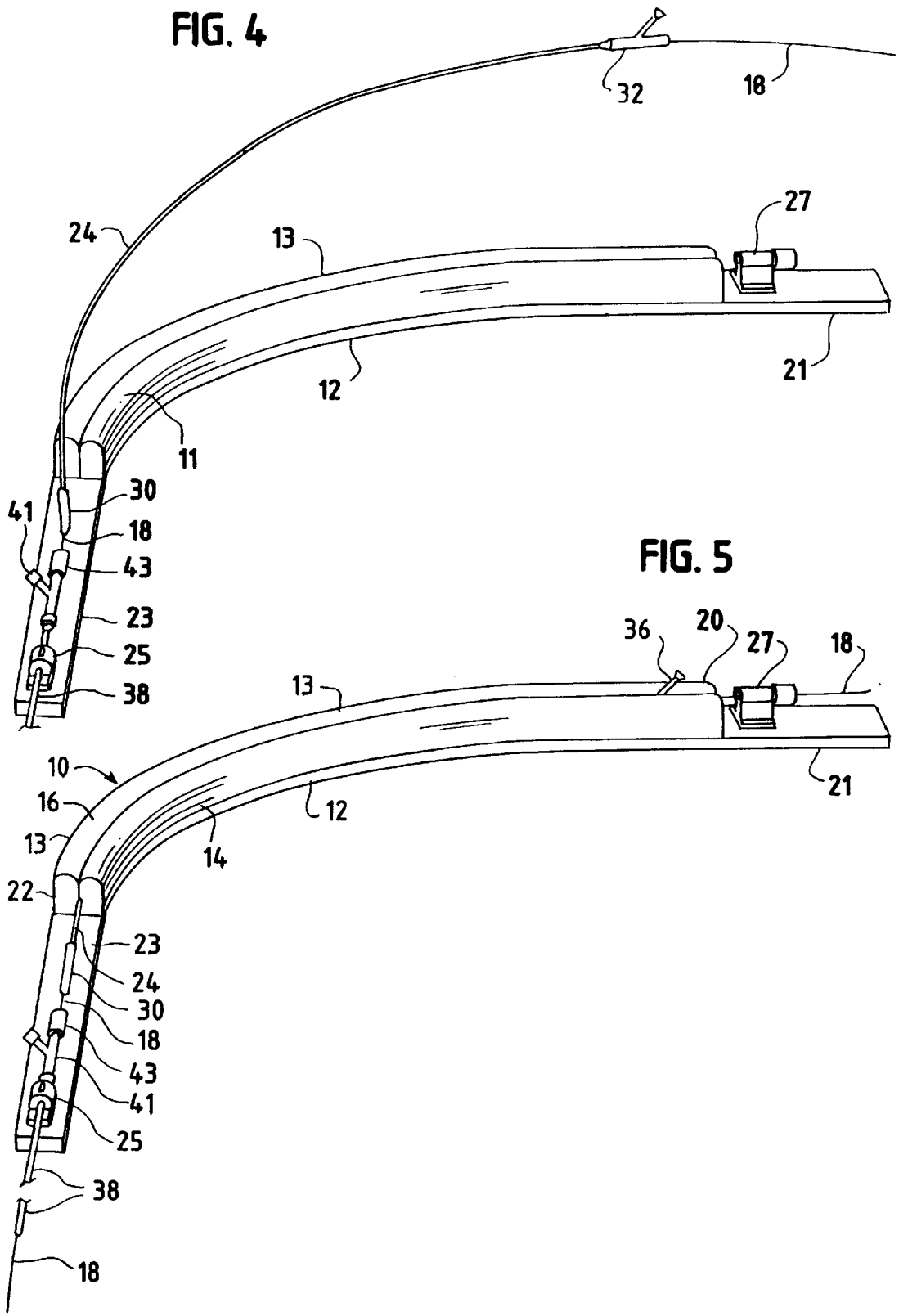

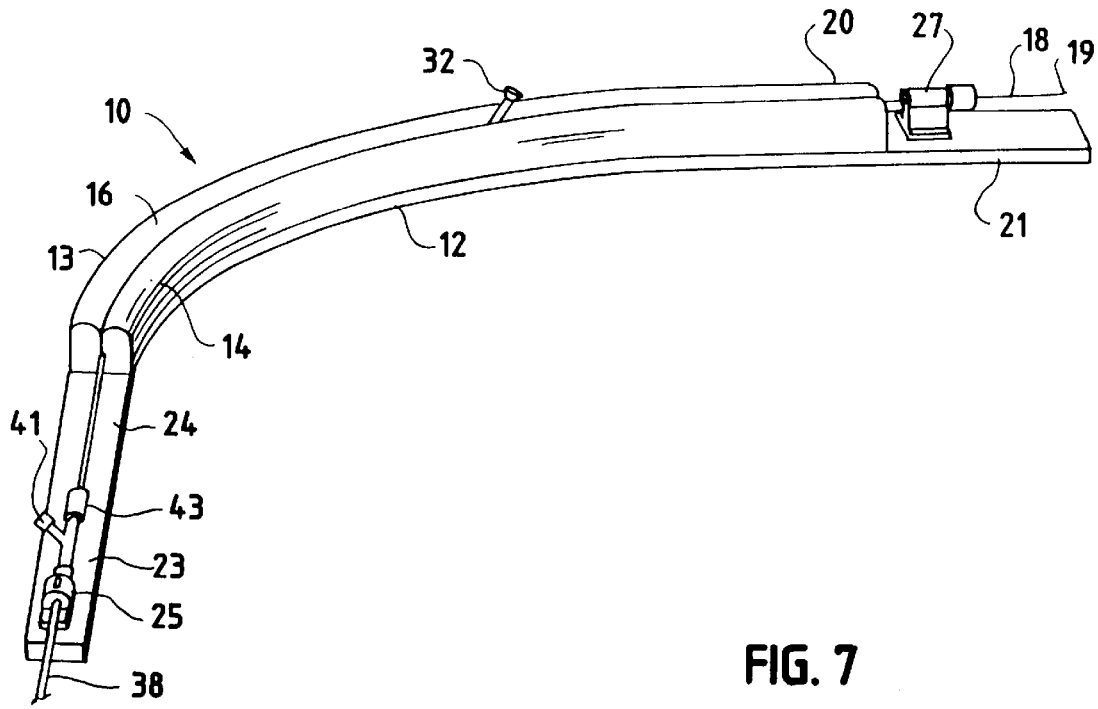
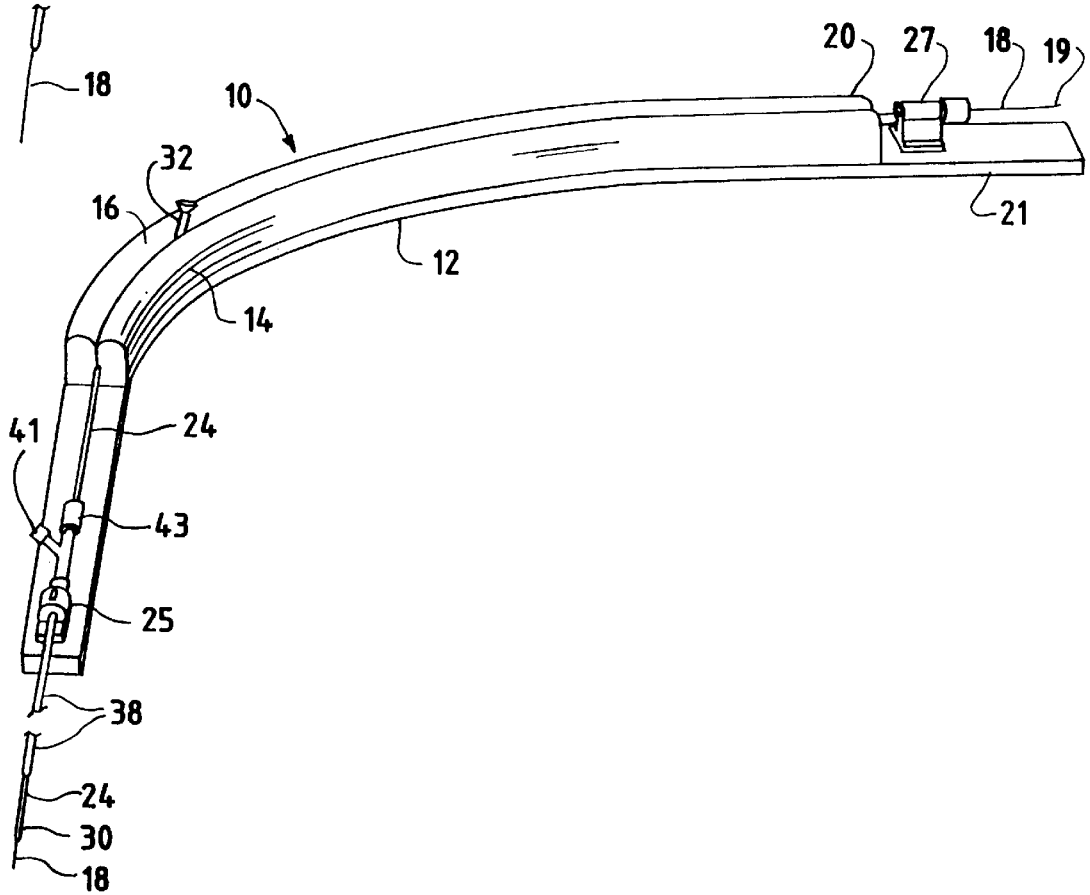

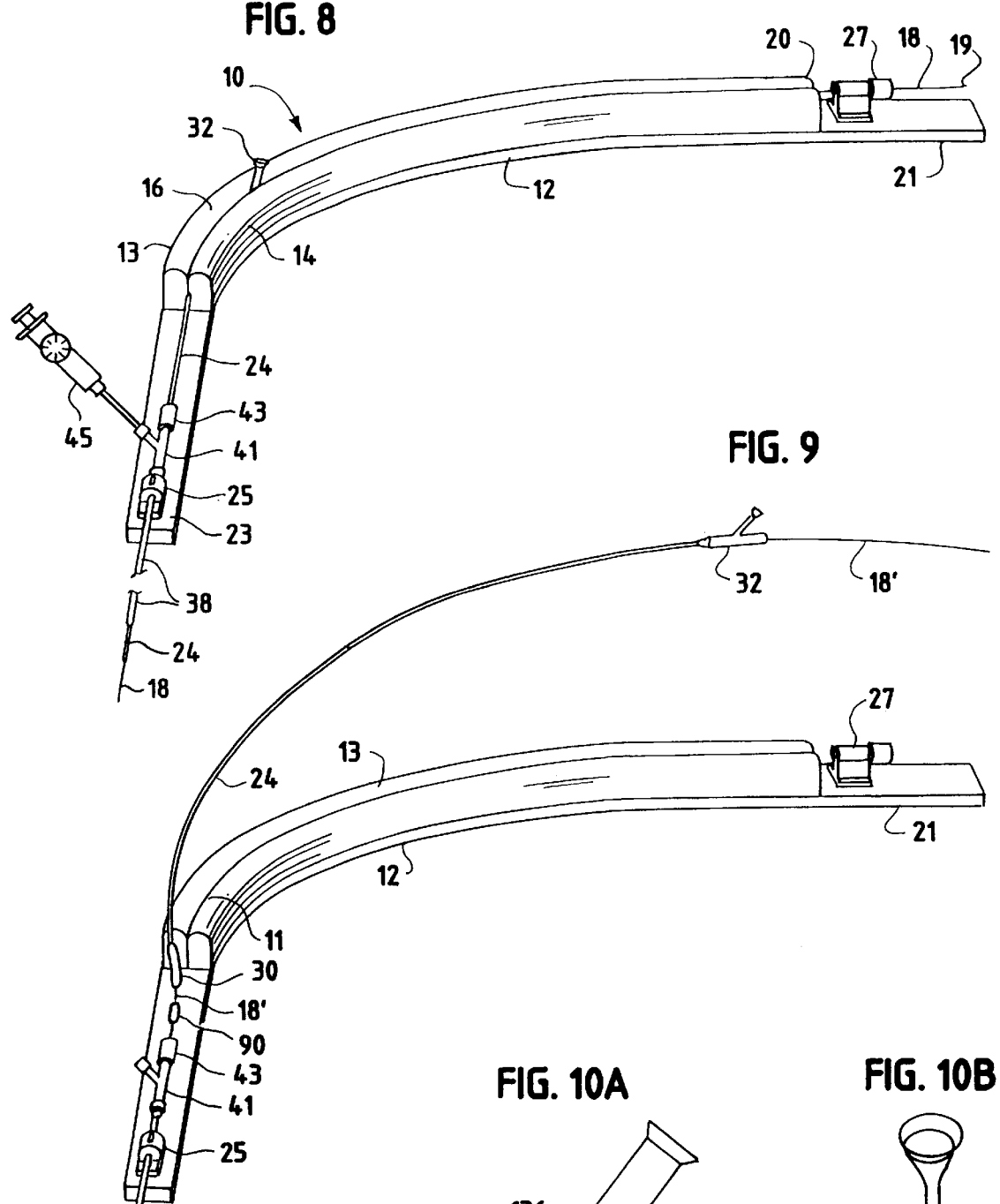

CATHETER EXCHANGE METHOD AND APPARATUS

BACKGROUND OF THE INVENTION

The present invention relates to the use and placement of flexible tubes, such as catheters, for the delivery or removal of instruments or substances in the body of a patient and, more particularly, to a new method and system to facilitate placement, withdrawal and of tubes exchange during dilation procedures such as angioplasty. While the present methods and apparatus of the present invention are designed for use in a variety of applications involving the insertion or removal of tubes in the body of a patient, the invention is discussed in terms of catheters used in the vascular system, by way of example.

Catheters are widely used for a variety of medical procedures involving insertion of catheters at various locations within a patient. Catheters are used in angioplasty procedures to open stenoses in the treatment of vascular diseases throughout the vascular system, including in the coronary arteries.

A typical angioplasty procedure involves the placement of a dilation catheter having an inflatable balloon in a deflated state at its end within the stenosis and then inflating the balloon causing it to radially expand the artery until the artery is re-opened to establish an acceptable rate of flow. The balloon is subsequently deflated and removed from the artery. In a similar procedure, a sleeve shaped deformable stent is deployed into the artery and radially expanded by inflation of a balloon positioned within. The stent remains in place in the artery after the balloon is deflated and removed to maintain flow in the artery.

The placement of the dilation or balloon catheter and the balloon usually involves the use of a guidewire which is advanced through the patient's vascular system to the location that is to be treated. In the typical angioplasty procedure for the coronary artery a guide catheter is introduced into the patient through the femoral artery and into the aorta, and then subsequently through the osteum to access the coronary artery. The guide catheter remains in place throughout the procedure to serve as a means for the guidewire and the balloon catheter to access the artery.

The balloon catheter is threaded onto the guidewire prior to insertion into the patient. The guidewire, which is typically made of stainless steel and platinum having a diameter of about 0.0100–0.018 inches, can be formed with a slight curvature at the end which enables the physician to steer the guidewire while advancing or withdrawing.

The balloon catheter is an elongated, flexible member having two longitudinal passages therethrough and a balloon at its distal end. One longitudinal passage provides a sleeve passage for receiving the guidewire. The other longitudinal passage provides a fluid or gas conduit for introducing pressurized fluid or gas from external pressurized means to the interior of the balloon to inflate the balloon. The two longitudinal passages may be provided adjacent to each other or in coaxial alignment whereby the inner passage receives the guidewire and the outer passage carries the pressurized inflation medium.

The guidewire is inserted through the balloon catheter such that a portion of the guidewire extends from the distal end of the balloon catheter and another portion extends from the proximal end. Together the guidewire and the balloon catheter are inserted into the proximal end of the guide catheter until the balloon reaches the distal end of the guide catheter. At this point, the physician holds the balloon catheter in position and, using fluoroscopy to view the procedure, pushes the guidewire past the distal end of the guide catheter, steering the guidewire into a selected artery. The guidewire is advanced until it reaches the desired area of treatment. The distal end of the guidewire is then pushed past the stenosis.

While holding the guidewire in place, the physician advances the balloon catheter along the guidewire. When the balloon reaches the area of the stenosis to be treated the inflation medium is injected through the balloon catheter and into the interior of the balloon. The resultant inflation of the balloon expands the inside wall of the artery in the region of the stenosis thus re-opening blood flow in the artery. Similarly, in stenting procedures, the inflation of the balloon expands and permanently deforms the stent so that the stent maintains a sufficient diameter opening in the artery for adequate blood flow.

Sometimes during angioplasty procedure it is necessary to use more than one balloon or stent to treat a blocked or dissected artery or to exchange a first balloon for a subsequent balloon of a different size. In order to carry out the exchange of a balloon catheter it is necessary to remove the balloon catheter by holding the guidewire in place and manually retrieving the catheter. The balloon catheter is withdrawn until it is completely out of the patient and past the proximal end of the guide wire. A new balloon catheter is then re-inserted over the guidewire and advanced until the balloon is positioned at the location of the area to be treated by the procedure described above.

PROBLEMS TO BE SOLVED

During various inter-vascular procedures such as angioplasty or stenting, especially during catheter exchange, it is desirable to leave the inserted guidewire in place because the presence of the guidewire in the artery may cause the artery to react by constricting. Also, predilated lesions can become dissected during angioplasty procedures. Thus, removal of the guidewire during such a constricted or dissected state may make re-insertion of the guidewire difficult or impossible. Throughout a procedure using a guidewire and catheter it is essential to maintain stable axial positioning of the guidewire tip to prevent inadvertent withdrawal of the guidewire from the area to be treated and to prevent inadvertent forward advancing of the guidewire which could cause damage to tissue or otherwise endanger the patient.

In order to remove or withdraw a balloon catheter while holding the guidewire in place, a difficult and time-consuming procedure must be followed. This is because in order to remove the balloon catheter from the guide catheter the proximal end of the guidewire must be held to prevent axial movement and buckling of the guidewire. Then the entire length of the balloon catheter must be withdrawn past the proximal end of the guide catheter, requiring the guidewire or an extension thereof to extend at least the length of the catheter beyond the proximal end of the guide catheter when the balloon catheter is inserted fully into the patient. Alternatively, the balloon catheter and guidewire must be held at the proximal end of the balloon catheter and moved together in very small incremental steps while the guidewire is pushed back into the patient by the same incremental amount between each step. Once the balloon catheter is advanced past the proximal end of the guide catheter, the guidewire can be grasped adjacent the proximal end of the guide catheter to allow quick removal of the balloon catheter. The balloon catheter is removed and a new one is inserted over the guidewire and advanced to the area to be treated, with the guidewire axially maintained in position. Such a procedure is cumbersome and, in some instances, poses an increased danger to the patient when time is especially critical.

The above-described procedure usually requires at least one assistant, and sometimes two, to assist the primary physician in manipulating the angioplasty system components. Due to the length of a typical guidewire and balloon catheter assembly, it is sometimes difficult for the physician to simultaneously reach and manipulate the angioplasty system components. At the same time, the physician must also maintain watch, via fluoroscopy, over the positioning of the components within the patient's body. Because of the need to manually move the guidewire and balloon catheter relative to each other as described above, with no secure means of fixing one or the other to a stationary point in the surrounding environment, approximations with respect to the positioning of each must be made by the person or persons moving each component. While this method is already prone to error when only one individual is handling both components, the likelihood of error is heightened when two or more individuals are assisting in coordinating the relative movement of the components. The need to accommodate additional personnel and to carefully synchronize their movement and accuracy adds to the complexity of the procedure, adding potential risks and danger.

In all procedures, including angioplasty, it is desirable to minimize radiation exposure to the patient, the physician and the attending staff that is attributable to the use of x-rays in fluoroscopy technology. The physician and staff are subject to cumulative radiation exposure over time. In angioplasty procedures, it is necessary to use a fluoroscope to visually monitor the relative positions of the guidewire and balloon or stent inside the patient's body with respect to each other and to the patient's body. If means were provided to reliably maintain the position of the guidewire relative to the patient, the fluoroscope would not need to be relied upon to monitor the guidewire position or the position of the balloon, until the balloon is positioned near the distal end of the balloon catheter. Up until that point, the physician, if provided with reliable means to secure the guidewire and prevent its buckling, could rely on the already commercially available length markings provided on certain balloon catheters that correspond to guide catheter length in order to know the relative position of the balloon.

It is therefore desirable to provide means and a method to quickly and safely install, remove or exchange balloon or dilation catheters using a guidewire.

Various known devices such as those described in U.S. Pat. No. 5,255,690 and U.S. Pat. No. 5,454,785 provide a hollow tube for guiding the withdrawal of catheters over guidewires. In those devices, however, semi-flexible materials having diameters sufficient to permit clearance for the catheter and the attached structure such as a Y-adapter are used for the tubes, resulting in lateral clearance around the enclosed guidewire. Such clearance allows lateral guidewire play and provides inferior support against buckling of the guidewire, which could disturb the position of the guidewire tip inside the patient. Also, such buckling may cause frictional forces between the guidewire and the inside wall of a balloon catheter, causing inadvertent withdrawal of the guidewire when the balloon catheter is removed. Furthermore, such known devices do not facilitate easy lateral installation of the guidewire into the guiding device during catheter exchange, which enables safe and rapid exchanges that are critical during such procedures. Instead, such devices require axial insertion of the hollow tube over the proximal end of the guidewire or guidewire extension.

It is therefore an object of the present invention to provide an apparatus and method for quickly, safely and accurately installing, removing or exchanging a catheter while avoiding the above-identified problems and shortcomings of the prior known devices.

SUMMARY OF THE INVENTION

The present invention is directed to an apparatus and associated method for installing, removing or exchanging catheters quickly and safely in various procedures including angioplasty and stenting. The apparatus of the present invention includes a guide track comprising an elongated base and a resilient, cushion-like body having a slot therein extending lengthwise. The base extends beyond the distal end of the body for mounting an appropriate clamping mechanism to attach the guide catheter to the apparatus. The slot is adapted to securely receive a catheter guidewire and to facilitate removal and placement of catheters on the guidewire. The slot formed in the guide track is adapted to physically conform to the outer shape of a guidewire and catheter to accommodate the passing through of a guidewire and catheter and related structures.

In operation, the guide track is positioned adjacent to the proximal end of a guide catheter inserted into a patient and having a guidewire and catheter held therein. Once the guide track is secured relative to the guide catheter and the guidewire or guidewire extension is relatively fixed thereto, the catheter can be slidingly removed or a new one can be inserted over and along the guidewire quickly and safely, without disrupting the position of the guidewire relative to the patient.

BRIEF DESCRIPTION OF THE DRAWINGS

FIG. 1 illustrates a guide track assembly of the present invention.

FIG. 2 illustrates a balloon catheter having a balloon and a y-adapter attached at a proximal end and an angioplasty balloon attached at a distal end, and further having a guidewire positioned therethrough.

FIG. 3 illustrates a guide catheter having a y-adapter at a proximal end, and receiving therethrough a balloon catheter and guidewire assembly of the type illustrated in FIG. 2.

FIG. 4 illustrates a guide track assembly as shown in FIG. 1, having a guide catheter as shown in FIG. 3 attached at the distal end of the guidetrack and further having a balloon catheter received over a guidewire and positioned laterally above the guide track assembly.

FIG. 5 illustrates the guide track assembly of the present invention having received therein a guide catheter, balloon catheter, and a guidewire, with the balloon catheter in a withdrawn position.

FIG. 6 illustrates the guide track assembly of FIG. 5 with the balloon catheter in an intermediate position between the withdrawn position of FIG. 5 and an inserted position.

FIG. 7 illustrates the guide track assembly of FIG. 5 with the balloon catheter in a fully inserted position.

FIG. 8 illustrates the guide track assembly of FIG. 7 having balloon inflation means attached.

FIG. 9 illustrates an optional detachable guidewire being utilized with the present invention guide track assembly.

FIGS. 10A–10B are side and front views of a novel, present invention y-adapter.

DESCRIPTION OF THE PREFERRED EMBODIMENT

The preferred embodiment of the method and apparatus of the present invention is disclosed in FIGS. 1–10 and described herein.

Referring to FIG. 1, a guide track 10 comprises a base 12 and a body 13 that is either unitary or that is made up of two parts, in either case forming first and second pad strips, shown at 14 and 16, respectively. In the case of either unitary or double body construction, the body 13, or bodies 14, 16, are fixed to the base by adhesive or other means. The body 13 has a slot opening 11 opening at its top surface and formed between the two pad strips 14, 16. The slot opening 11 is adapted to receive a catheter guidewire 18 and balloon catheter 24 as described below with reference to FIGS. 4–9. The body 13 has a proximal end 20 and a distal end 22. At the distal end 22, an extending base 23 has a catheter clamp 25 for selectively securing a guide catheter 38 thereto, as described below with reference to FIGS. 4–9. At the proximal end 20, an extending base portion 21 has a guidewire clamp 27 mounted thereon for selectively securing a guidewire 18. The clamp 27 may be of any conventional type. It is preferable, however, that the clamp 27 be of a slotted, lateral-entry type having rotatable tightening means for placing the guidewire 18 laterally and ensuring adequate gripping thereof.

The base 12 of the body 13 is preferably made from a generally flat, elongated semi-flexible material or a combination of wire-core and flexible polymer to enable deformation to a desired shape that lays generally within the X-Y plane, in accordance with the X-Y-Z axes shown in FIG. 1. While the base is semi-rigid with respect to the Z-direction, it does not rigidly maintain a strict co-planar relationship with the X-Y plane. By allowing some flexibility of the base 12 with respect to the Z-direction, the guide track 10 can be positioned and maintained on a variety of surfaces and remain functional. By being generally more flexible within the X-Y plane, the guide track 10 can be configured into an "S-curve" or a "J-shape", or various other desirable shapes, if necessary to accommodate the surrounding environment.

The body 13 of the guide track 10 has two sections defined by the longitudinally-aligned slot opening 11 that extends from the proximal end 20 to the distal end 22. In the preferred embodiment the body 13 is unitary and has two elongated pad strips 14, 16 that contact each other, forming the slot opening 11 at their respective areas of contact with one another. Alternatively, the body 13 can be comprised of a two elongated members similar to pad strips 14 and 16 and being positioned adjacent to each other to form a slot therebetween to define the slot opening 11. The two sections, or the pad strips 14 and 16 in the preferred embodiment, are resilient and cushion-like such that they can be deformed at the location of externally applied pressure but will return to original form when the applied pressure is removed. In a resting state, the inner walls of the two strips 14 and 16 are in contact with each other at the slot 11.

The pad strips 14, 16 can be formed of any flexible material such as foam, or a closed-cell system of liquid, gel or air. In the preferred embodiment the pad strips 14, 16 comprise a closed-cell system formed by a vinyl or similar skin having gel or a viscous liquid contained therein. The slot 11 and the pad strips 14, 16 should be configured so that when a conventional catheter guidewire 18 is positioned within the slot 11, the inner walls of the slot 11 close in around the guidewire 18, making contact therewith, as shown in FIG. 1. It is preferable that the exterior surface of the body 13, particularly inside the slot 11, is relatively smooth to minimize sliding friction between the balloon catheter 24 and the slot 11 surfaces.

A conventional balloon angioplasty system is shown in FIG. 2. The system comprises a balloon catheter 24 having distal and proximal ends shown at 26 and 28, respectively.

The balloon catheter 24, which is adapted to be threaded over the guidewire 18 as shown, has a balloon 30 at its distal end 26. At the proximal end 28 of the balloon catheter 24 there is a Y-adapter 32 having a first open end 33 and a second open end 34, each aligned with the other forming a passage and adapted to receive the guidewire 18 therethrough. The Y-adapter 32, which may be of a conventional type such as TOUHY-BORST, is provided with an open secondary extension 36. The secondary extension 36 forms a conduit that cooperates with the first and second open ends 33, 34. The secondary extension extends away from the longitudinal axis of the Y-adapter which is aligned generally with the passage formed by the first and second open ends 33, 34.

As shown in FIG. 3, a conventional guide catheter 38 having an end adapter 39 and a y-adapter 41 at the proximal end is provided. In typical use, the guide catheter 38 is inserted into the patient's vascular system prior to insertion of the angioplasty system illustrated in FIG. 2, such that the end adapter 39 remains extending out of the patient. The guidewire 18 is threaded through the guide catheter 38 until the distal end 17 reaches a desired location, while the proximal end 19 of the guidewire 18 remains extending out of the patient. The guidewire 18 can be clamped internally and relative to the guide catheter 38 by securing a rotatable clamp 43 which, with typical y-adapters, is integral to the y-adapter 41. Once the distal end 17 of the guidewire 18 is in the desired location, the balloon catheter 24 with the attached balloon 30 is deployed into the patient over the guidewire 18 and inside the guide catheter 38. The balloon catheter 24 is moved until the balloon 30 is in a desired location. Upon positioning the balloon 30, a portion of the balloon catheter 24 proximal end 28 and the Y-adapter 32 will remain extending out of the patient, and thus adjacent the end adapter 39 and y-adapter 41 of the guide catheter 38 as shown in FIG. 3.

In the preferred embodiment, it is desirable to provide a guidewire 18 of sufficient length so that portion 19 extending out of the patient is longer than the balloon catheter 24. If necessary, it is possible to selectively lengthen a guidewire 18 using a conventional guidewire extension and coupling system, described below with reference to FIG. 9. Such a system would include a coupling device for enabling an extension wire to be joined coaxially with the guidewire 18.

When insertion of a balloon catheter into a patient is desired, the guide track 10 is positioned as shown in FIG. 4. The distal end extending portion 23 of the base 12 is positioned to receive the proximal end of the guide catheter 38 in the guide catheter clamp 25. The clamp 25 holds the guide catheter 38 such that the end adapter 39 and y-adapter 41 are positioned toward the proximal end of the track 10 with respect to the clamp 25. The rotatable clamp portion 43 can be tightened around the guidewire 18 to maintain the guidewire's position relative to the guide catheter (38).

The balloon catheter 24, having the guidewire 18 threaded therethrough, can be lowered laterally into the slot 11 on the track body 13 until it is positioned as shown in FIG. 5. At that time, the guidewire clamp 27 on the proximal end base portion 21 can be tightened to grip the guidewire 18 as shown. Having secured the guidewire clamp 43 of the guide catheter 38, as well as the guidewire clamp 27 or the proximal base portion 21, and having positioned the balloon catheter 24 with guidewire 18 into the slot 11, there should be no slack or buckling of the balloon catheter 24 or guidewire 18.

The y-adapter 32 of the balloon catheter 24 is positioned in the slot 11 such that the secondary extension 36 remains protruding out of the slot 11 as shown in FIG. 5. The protruding portion of the secondary extension 36 provides a portion that the physician can grasp with his fingers to move the balloon catheter 24 into or out of the patient, while maintaining the balloon catheter 24 and guidewire 18 in the slot 11. It is understood that any other type of tab or extension connected to the balloon catheter 24 or the y-adapter 32 can serve this purpose.

When the physician is ready to advance the balloon catheter 24 into the patient, the clamp 43 is released from around the guidewire 18 while the balloon catheter 24 is in the position shown in FIG. 5. The physician can advance the balloon catheter 24 into the patient by grasping the balloon catheter 24 at a location near the distal extending portion 23 of the base 12, between the clamp 43 and the distal end 22 of the track body 13, and then by advancing the balloon catheter 24 along the guidewire 18 toward the distal end 17 of the guidewire 18. As shown in FIG. 6, the y-adapter 32, being attached to the balloon catheter 24, is advanced toward the patent as the balloon 30 and catheter 24 enter the patient through the guide catheter 38.

Using fluoroscopy or other known means to internally view the position of the balloon in the patient, the physician can selectively monitor the positioning of the balloon 30 until the balloon is positioned over the area to be treated. When the balloon 30 is positioned as desired, the y-adapter 32 and a portion of the balloon catheter 24 remain in the slot 11 as shown in FIG. 7. If desired, the guide catheter clamp 43 can be tightened to a desired degree around the balloon catheter 24. Once in position, the physician can utilize the y-adapter 32 to attach an inflation source 45 to inflate the balloon 30, or other devices as desired.

If it is desired to remove or exchange a balloon catheter 24, the procedure generally involves a reverse process of the above-described insertion procedure. To initiate removal of a balloon catheter 24, the physician, after having released the guide catheter clamp 43 as necessary, grasps the y-adapter extension 36 and withdraws it and the attached catheter 24 back toward the proximal end 20 of the track body 13. This is being carried out with the guidewire clamp 27 still securing the proximal end 19 of the guidewire 18.

Once the balloon catheter 24 is withdrawn such that the balloon 30 is removed from within the guide catheter 38 as shown in FIG. 5, the guide catheter clamp 43 is activated to secure the guidewire 18. Next, the guidewire clamp 27 is released to allow the guidewire proximal end 19 to be lifted up and out of the slot 11 of the track body 13. As the guidewire 18 is lifted out of the track slot 11, the balloon catheter 24 threaded thereon is also removed. The assembly is then positioned as shown in FIG. 4, so that the balloon catheter 24 can quickly be slid off the end of the guidewire 18 and, if desired, a new one can be threaded thereon for insertion as described above.

As disclosed in FIG. 9, an optional guidewire extension system can be used with the present invention track and exchange system. The extension system comprises a guidewire coupler 90 being adapted to connect to or having attached thereto a guidewire extension 18'. The coupler 90 is adapted to attached to the proximal end of a guidewire that is already inserted into a patient. The extension system can be used in situations in which the original guidewire 18 already inserted into the patient is of insufficient length to extend to the proximal end of the guide track body 13 to be attached by clamp 27 for use with the present invention. Alternatively, a pre-loaded guidewire extension assembly complete with a guidewire extension 18' and a balloon catheter 24 can be pre-installed in a track body 13 of the present invention for quick attachment of a guidewire 18 already installed in a patient. Then, when removal or exchange is desired, the entire assembly can be detached and, if desired, a new one can be re-attached without having to place or remove the guidewire 18' and balloon catheter 24 laterally with respect to the slot 11.

FIGS. 10A–10B illustrate a novel y-adapter 132 that can be used alternatively with the present invention catheter introduction and exchange apparatus and method. The y-adapter 132 has an extension portion 136 that is of a generally flat profile when viewed from the front, as in FIG. 10B, to enable low-resistance translation through the track slot 11 of the present invention. Furthermore, if desired, the ends 137, 138 can be rounded as shown in FIG. 10B to further reduce resistance during movement within the slot 11. It is recognized that the rounded ends 137, 138 and the flat profile extension 136 are features that can be used separate and apart from each other and that FIGS. 10A–10B illustrate by way of example only one of several novel combinations according to the present invention.

While the preferred embodiment of the invention has been herein disclosed and described, it is understood that modification and variation of the various components and procedural steps can be made without departing from the scope of the presently claimed invention. For instance, it is acknowledged that the present invention can be practiced with balloon catheters that are equipped with secondary conduit means or structural extensions for manipulating the catheter that vary from the specifically described Y-adapter. It is further understood that the guide track 10 can be used for removing, installing or exchanging a variety of guidewires and catheters in procedures not limited to balloon angioplasty.

While the preferred embodiment of the present invention has been herein described, it is understood that modifications and variations may be undertaken without departing from the scope of the presently claimed invention.

I claim:

1. An apparatus for guiding an elongated, hollow flexible member, said hollow flexible member having a wire received therethrough, said apparatus comprising
   a generally elongated base;
   a body attached to said base;
   wire attaching means for selectively attaching said wire relative to said base; and
   a slot in said body extending generally longitudinally and adapted to receive said hollow flexible member to guide said hollow flexible member during movement of said flexible member relative to said wire.

2. An apparatus according to claim 1, wherein
   said body is made of a soft, flexible material adapted to conform to said flexible member as it is moved within said slot.

3. An apparatus according to claim 1, wherein
   said base and said body are flexible and adapted to be selectively deformed with respect to at least two orthogonal planes.

4. An apparatus for guiding a catheter tube along a guidewire received therein, said apparatus comprising
   a generally elongated base;
   a body attached to said base;
   guidewire attaching means for selectively attaching said guidewire to said apparatus such that said catheter tube can be moved relative to said guidewire while said guidewire remains stationary with respect to said base; and a slot in said body adapted to receive said catheter tube and said guidewire to guide said catheter tube during movement thereof.

5. An apparatus according to claim 4, wherein
said body is made of a soft, flexible material adapted to conform to said catheter tube as it is moved within said slot.

6. An apparatus according to claim 4, wherein
said base and said body are flexible and adapted to be selectively deformed with respect to at least two orthogonal planes.

7. An apparatus according to claim 4, further comprising
attaching means adapted to attach said base to a guide catheter inserted into the body of a patient.

8. An apparatus according to claim 4, wherein
said generally elongated base has a distal end and a proximal end, whereby a front extending base portion extends from said distal end and has guide catheter clamp means for selectively attaching a guide catheter to said base.

9. An apparatus according to claim 4, wherein
said body comprises a unitary, closed-cell chamber containing gas or liquid under pressure.

10. An apparatus according to claim 4, wherein
said body comprises a unitary, closed-cell chamber containing gel.

11. An apparatus according to claim 4, wherein
said body comprises two elongated strips, each strip comprising a unitary, closed-cell chamber containing gas or liquid under pressure, whereby said strips are placed against each other such that the area between them forms said slot.

12. An apparatus according to claim 4, wherein
said body comprises two elongated strips, each strip comprising a unitary, closed-cell chamber containing gel, whereby said strips are placed against each other such that the area between them forms said slot.

13. A catheter insertion and removal system for use with a guidewire having a proximal end and a distal end in which said distal end is inserted into the body of a patient and said proximal end remains extending out of said body of said patient, said system comprising
a first catheter tube having a passage therethrough and a longitudinal axis, a proximal end, and a distal end, said passage being adapted to receive said guidewire therethrough;
a guide catheter tube having a passage therethrough and a longitudinal axis, a proximal end, and a distal end, said distal end of said guide catheter being inserted into said body of said patient and said proximal end extending out of said body of said patient, wherein said guidewire extends through said guide catheter passage, and said guide catheter passage is adapted to receive said first catheter tube therein;
an elongated track having a proximal end and a distal end, and further having base and a body, said body being made of a resilient material and having a slot formed therein adapted to receive said first catheter tube and said portion of said guidewire that extends out of the body of said patient; and
guidewire attaching means for selectively attaching said guidewire to said proximal end of said track when said guidewire is positioned in said slot of said track and said distal end of said track is positioned adjacent to said body of said patient, whereby said catheter tube can be slidingly inserted into or removed from said body of said patient along said guidewire and within said guide catheter without causing buckling of said guidewire or longitudinal movement of said guidewire relative to said body of said patient.

14. A system according to claim 13, wherein
said body of said track is made of a soft, flexible material adapted to conform to said first catheter tube as it is moved within said slot.

15. A system according to claim 13, wherein
said base and said body of said track are flexible and adapted to be selectively deformed with respect to at least two orthogonal planes.

16. A system according to claim 13, further comprising
guide catheter attaching means adapted to attach said guide catheter to said track while said guide catheter is inserted into the body of said patient.

17. A system according to claim 16, wherein
said guide catheter attaching means comprise a clamp mounted on a generally elongated front extension of said track base that extends from the distal end of said track body.

18. A system according to claim 13, wherein
said guidewire attaching means comprise a clamp mounted on a generally elongated rear extension of said track base that extends from the proximal end of said track body.

19. A system according to claim 13, wherein
said proximal end of said guidewire that remains extending out of said body of said patient comprises a selectively attachable guidewire extension adapted to attach coaxially to said guidewire at a location out of said body of said patient.

20. A catheter insertion and removal system for use with a guidewire having a proximal end and a distal end in which said distal end is inserted into the body of a patient and said proximal end remains extending out of said body of said patient, said system comprising
a selectively attachable guidewire extension having a proximal end which is adapted to attach coaxially to said guidewire, and a distal end;
a first catheter tube having a passage therethrough and a longitudinal axis, a proximal end, and a distal end, said passage being adapted to receive said guidewire and said guidewire extension therethrough;
a guide catheter tube having a passage therethrough and a longitudinal axis, a proximal end, and a distal end, said distal end of said guide catheter being inserted into said body of said patient and said proximal end extending out of said body of said patient, wherein said guidewire extends through said guide catheter passage, and said guide catheter passage is adapted to receive said first catheter tube therein;
an elongated track having a proximal end and a distal end, and further having base and a body, said body being made of a resilient material and having a slot formed therein adapted to receive said first catheter tube and said guidewire extension, and
guidewire attaching means for selectively attaching said guidewire extension to said proximal end of said track when said guidewire is positioned in said slot of said track;
whereby said guidewire extension is pre-loaded in said first catheter tube and said first catheter tube is positioned in said slot with said guidewire extension attached to said track by said guidewire attaching means such that when insertion or removal of said first catheter tube into or out of said patient is desired, said guidewire extension is attached to said guidewire thereby enabling said first catheter tube to be slidingly inserted into or removed from said body of said patient along said guidewire and within said guide catheter without causing buckling of said guidewire or longitudinal movement of said guidewire relative to said body of said patient.

* * * * *